US00PP28979P2

(12) United States Plant Patent
Van Swieten

(10) Patent No.: US PP28,979 P2
(45) Date of Patent: Feb. 20, 2018

(54) ***PHALAENOPSIS* ORCHID PLANT NAMED 'PHALDTYK'**

(50) Latin Name: ***Phalaenopsis* hybrid**
Varietal Denomination: PHALDTYK

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 7 days.

(21) Appl. No.: 15/330,034

(22) Filed: Jul. 28, 2016

(51) Int. Cl.
*A01H 5/02* (2006.01)

(52) U.S. Cl.
USPC ..... Plt./311

(58) Field of Classification Search
USPC ..... Plt./311
See application file for complete search history.

(56) References Cited

PUBLICATIONS

UPOV-PLUTO: Plant Variety Database, citation for 'PHALDTYK'; Internet retrieval Sep. 25, 2017.*
EU Community Plant Variety Rights Application No. 2016/0956, Application n°A201600635, filed Apr. 18, 2016, 8 pages.
EU Community Plant Variety Office Official Gazette, 3.2016, Jun. 15, 2016, cover page and pp. 35, 52.

* cited by examiner

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALDTYK', particularly characterized by having light purple shaded flowers, 1 to 3 peduncles that are long and sturdy, leaves that are obovate, and is propagated by meristem tissue culture, is disclosed.

3 Drawing Sheets

Genus and species: *Phalaenopsis* hybrid.
Variety denomination: 'PHALDTYK'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALDTYK'.

The new *Phalaenopsis* plant is a product of a planned breeding program conducted by the inventor in Bleiswijk, The Netherlands. The objective of this breeding program was to create a new *Phalaenopsis* plant with numerous attractive and unique light purple shaded flowers, suitable for potted plant production.

The new *Phalaenopsis* plant 'PHALDTYK' is a result of cross-pollination made by the inventor in July 2005 in Bleiswijk, The Netherlands of the proprietary female, or seed parent, *Phalaenopsis* hybrid '22790-01' (unpatented) with the proprietary male, or pollen parent, *Phalaenopsis* hybrid '7693-020' (unpatented).

The new *Phalaenopsis* was selected by the inventor as a single plant within the progeny of the stated cross-pollination in a controlled greenhouse in Bleiswijk, The Netherlands in October 2008. Asexual reproduction of the new *Phalaenopsis* plant by meristem tissue culture since 2011 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 18, 2016. 'PHALDTYK' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALDTYK' as a new and distinct variety of *Phalaenopsis* plant.

1) Light purple shaded flowers;
2) 1 to 3 peduncles;
3) Peduncle is long and sturdy; and
4) Shape of the leaf is obovate.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in June 2016. Colors in the photographs may differ from the color values cited in the detailed botanical description, which accurately describe the actual colors of the new variety.

DESCRIPTION OF THE NEW VARIETY

Figure 1:
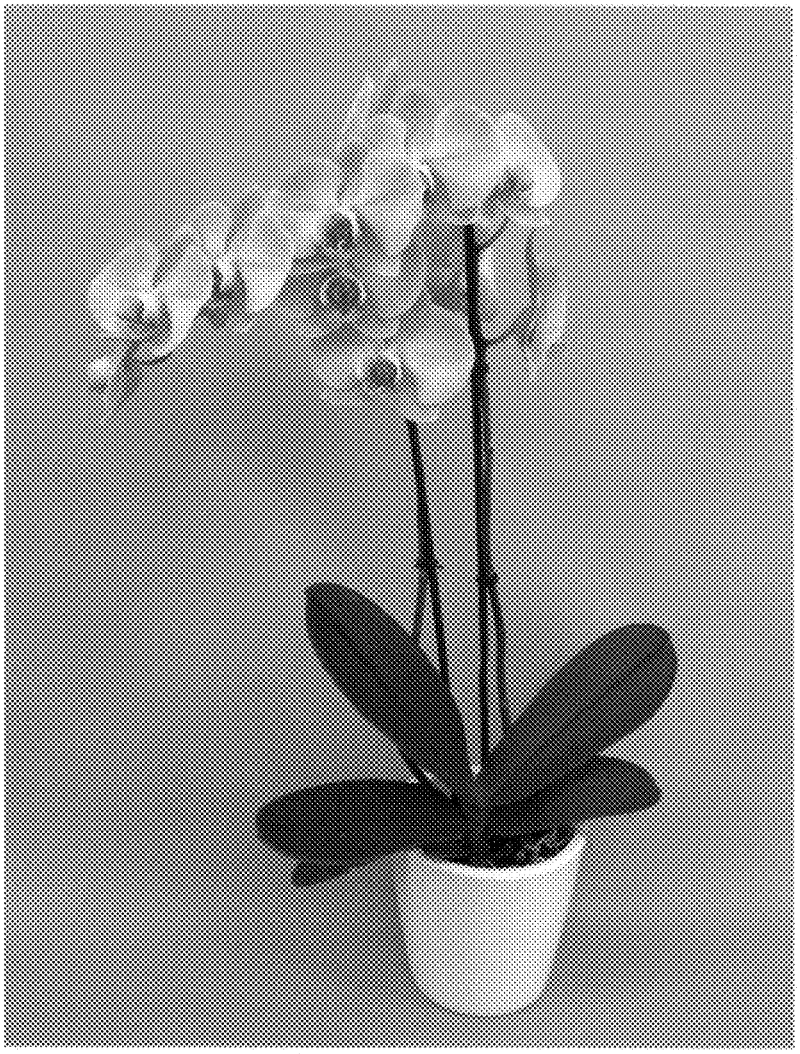
FIG. 1 shows the overall plant habit, including blooms and foliage of 'PHALDTYK'.
Figure 2:
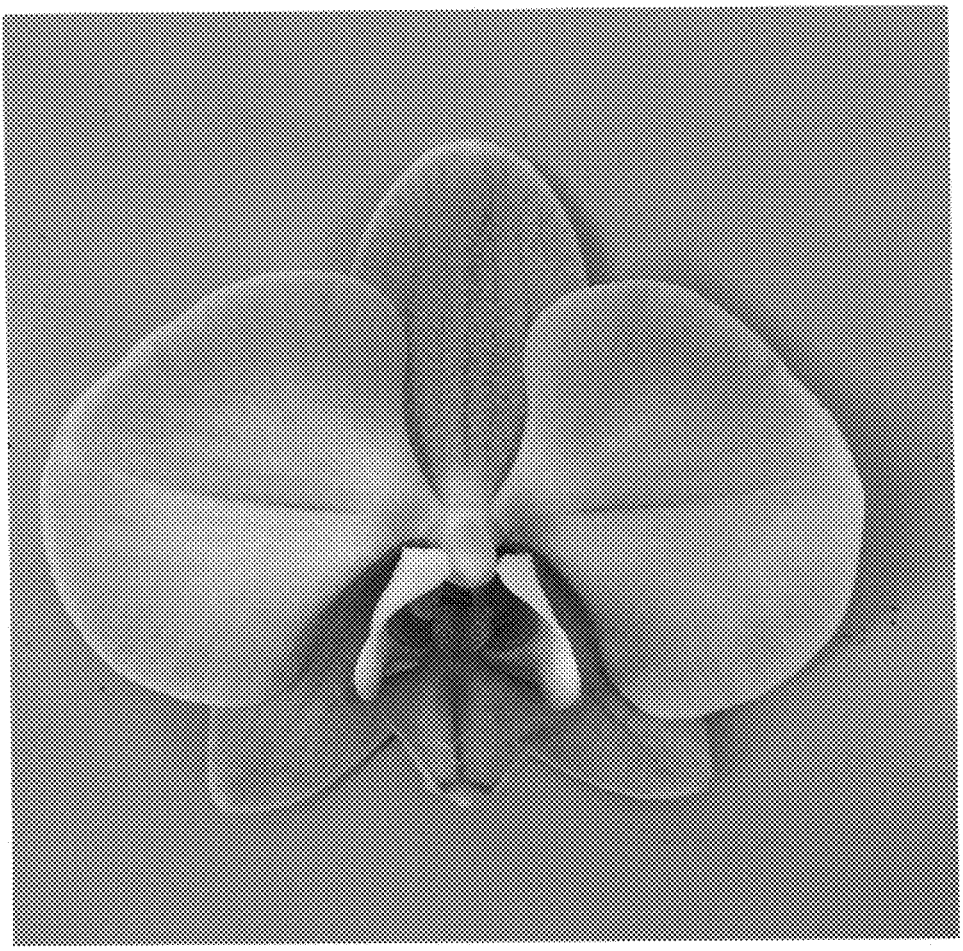
FIG. 2 shows a close-up of a flower of 'PHALDTYK'.
Figure 3:
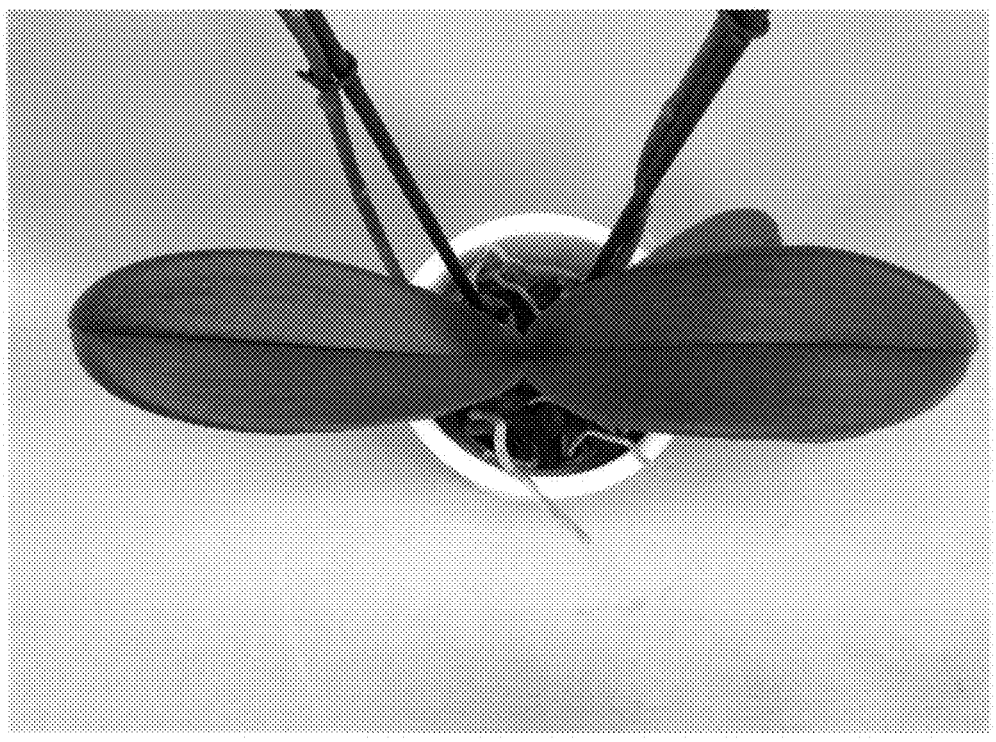
FIG. 3 shows a close-up of the leaves of 'PHALDTYK'.

The following detailed description sets forth the distinctive characteristics of 'PHALDTYK'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in June 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALDTYK'.

Parentage:

*Female parent*.—*Phalaenopsis* cultivar '22790-01' (unpatented).

*Male parent*.—*Phalaenopsis* cultivar '7693-020' (unpatented).

Propagation:

*Type*.—Meristem tissue culture.

Roots:

*Root description*.—Greyed-green colored roots with lightly branching lateral roots having greyed-purple colored root tips.

Plant:

*Commercial crop time to flowering*.—Approximately 48 to 50 weeks from a rooted cutting to finish in a 12 cm pot.

*Growth habit of peduncle*.—Standard, green leaves, raceme.

*Height* (*from soil level to top of inflorescence*).—Approximately 40.0 cm to 50.0 cm.

*Width* (*measured from leaf tips*).—About 34.0 cm to 39.0 cm.

*Vigor*.—Strong.

Leaves:

*Mature leaves*.—Quantity per plant: 6 to 8 leaves are produced before flowering. Length (fully expanded): 17.0 cm to 21.0 cm. Width: 7.0 cm to 8.0 cm. Shape: Obovate. Base shape: Moderately elongated. Apex: Obtuse unequal. Leaf blade angle with the petiole (measured from the horizontal position): Between 0 degrees and 30 degrees. Leaf margin: Entire. Color: Upper surface: RHS 146A. Lower surface: RHS 146B. Texture: Rough. Thickness: 2.5 mm to 2.9 mm. Venation: Pattern: Parallel. Color of the midvein: Upper surface: RHS 147A. Lower surface: RHS 146A.

Peduncle:

*Quantity per plant*.—1 to 3.

*Number of flowers per peduncle*.—8 to 12.

*Length*.—40.0 cm to 50.0 cm.

*Diameter*.—5.1 mm to 5.4 mm.

*Strength*.—Strong.

*Aspect*.—Upright to slightly pendant.

*Texture*.—Slightly rough.

*Color*.—Green (RHS 146A), and dark purple (RHS 187A) bracts along the peduncle.

*Internode length*.—3.0 cm to 4.0 cm.

*Callosities*.—None.

Inflorescence description:

*Appearance*.—Upright to slightly pendant, raceme inflorescence with bilaterally symmetrical flowers that open in succession beginning with the lowermost flower.

*Inflorescence size*.—Height (from base to tip): 180.0 mm to 220.0 mm.

*Flowering time*.—First flowers can be expected 10 to 11 months after planting in a 12 cm (diameter) pot.

*Flower*.—Height: 87.0 mm to 89.0 mm. Diameter: 95.0 mm to 97.0 mm. Depth of lip: 25.0 mm to 27.0 mm.

*Flower longevity*.—On the plant: 10 to 14 weeks.

*Fragrance*.—Absent.

*Flower bud*.—Length: 22.0 mm to 24.0 mm. Width: 20.0 mm to 22.0 mm. Shape: Egg shaped. Color: Mix of dark purple (RHS 187C) and green (RHS 146C).

*Petals*.—Arrangement: Open/free. Shape: Semi-circular. Apex: Rounded asymmetric. Margin: Entire. Length (from base to tip): 44.0 mm to 46.0 mm. Width: 56.0 mm to 58.0 mm. Color (when fully opened): Upper surface: Basic color: Light purple (RHS 76C). Over color: Purple (RHS N80D). Lower surface: Basic color: Light purple (RHS 76B). Over color: Purple (RHS N78D).

*Dorsal sepal*.—Shape: Elliptic. Apex: Rounded symmetric. Margin: Entire. Length (from base to tip): 47.0 mm to 49.0 mm. Width: 32.0 mm to 34.0 mm. Color (when fully opened): Upper surface: Basic color: Light purple (RHS 76C). Over color: Purple (RHS N78D). Lower surface: Basic color: Light purple (RHS 76B). Over color: Purple (RHS N78D).

*Lateral sepals*.—Shape: Ovate. Apex: Obtuse asymmetric. Margin: Entire. Length (from base to tip): 47.0 mm to 49.0 mm. Width: 28.0 mm to 30.0 mm. Color (when fully opened): Upper surface: Basic color: Light purple (RHS 76C). Over color: Light green (RHS 145D) at the base and purple (RHS 84B). Lower surface: Basic color: Light purple (RHS 84B). Over color: Purple (RHS N78D) and green (RHS 145D) at the base.

*Labellum* (*lip*).—Whiskers: Present. Length of whiskers: 24.0 mm to 26.0 mm. Color of whiskers: Orange (RHS 167A) with yellow tips (RHS 10A). Pubescence on the lip: Absent.

*Lateral lobe*.—Shape: Spatulate. Margin: Undulated. Length (from base to tip): 23.0 mm to 25.0 mm. Width: 18.0 mm to 20.0 mm. Color: White (RHS NN155C) with red (RHS 46A) at the base and yellow on one side (RHS 13B).

*Apical lobe*.—Shape: Triangular. Margin: Entire. Length: 19.0 mm to 21.0 mm. Width: 29.0 mm to 31.0 mm. Color: Red (RHS 185A) stripe in the middle with red (RHA 185A) and yellow-orange (RHS 16B) at the base and light purple (RHS 75C) towards the whiskers.

*Callus*.—Average size: Medium to large. Height: 0.6 cm to 0.7 cm. Length: 0.6 cm to 0.7 cm. Width: 0.4 cm to 0.5 cm. Color: Yellow-orange (RHS 17A) and dotted/striped (RHS 178B).

*Reproductive organs.*—Column: Length: 9.0 mm to 11.0 mm. Diameter: 5.9 mm to 6.2 mm. Color: Light purple (RHS N80D). Pollinia: Quantity: 2. Diameter: 1.0 mm to 1.2 mm. Color: Orange (RHS 26A). Ovary: Length: 9.0 mm to 11.0 mm. Diameter: 2.4 mm to 2.6 mm. Pedicel: Length: 32.0 mm to 34.0 mm. Diameter: 2.6 mm to 2.8 mm. Color: Mix of light purple (RHS N75A/B) and green (RHS 145D).

Disease, pest, and stress resistance: No specific resistance or susceptibility observed to pathogens and pests common to *Phalaenopsis.*

Fruit and seeds: Fruit and seed development has not been observed on plants of the new *Phalaenopsis.*

COMPARISON WITH PARENTAL AND COMMERCIAL VARIETIES

The female parent of 'PHALDTYK', cultivar '22790-01' (unpatented), is no longer in existence, so a meaningful comparison cannot be made.

The male parent of 'PHALDTYK', cultivar '7693-020' (unpatented), is no longer in existence, so a meaningful comparison cannot be made.

'PHALDTYK' is most similar to the commercial *Phalaenopsis* plants named 'PHALBARBOK' (unpatented) and 'PHALMACHE' (unpatented). 'PHALDTYK' differs from the commercial variety 'PHALBARBOK' in that 'PHALDTYK' has evenly colored lateral sepals, a light purple column and orange whiskers with yellow tips, whereas 'PHALBARBOK' has dotted lateral sepals, a purple column and pale purple whiskers. Additionally, 'PHALDTYK' has longer whiskers than 'PHALBARBOK'.

'PHALDTYK' differs from the commercial variety 'PHALMACHE' in that 'PHALDTYK' has flowers with a shaded pattern, evenly colored lateral sepals, a light purple column, orange whiskers with yellow tips and a rounded petal apex, whereas 'PHALMACHE' has flowers with a centered pattern, striped lateral sepals, a purple column, purple whiskers and an emarginated petal apex. Additionally, 'PHALDTYK' has longer whiskers and narrower petals than 'PHALMACHE'.

I claim:

1. A new and distinct variety of *Phalaenopsis* plant named 'PHALDTYK', substantially as described and illustrated herein.

* * * * *